United States Patent
Shumer et al.

(10) Patent No.: US 10,327,932 B2
(45) Date of Patent: *Jun. 25, 2019

(54) CATHETER HAVING HYDRAULIC ACTUATOR AND LOCKING SYSTEM

(71) Applicant: ABBOTT CARDIOVASCULAR SYSTEMS INC., Santa Clara, CA (US)

(72) Inventors: Daniel H. Shumer, San Jose, CA (US); Michael L. Green, Pleasonton, CA (US); Patrick C. Saxton, Santa Clara, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 470 days.

This patent is subject to a terminal disclaimer.

(21) Appl. No.: 15/016,520

(22) Filed: Feb. 5, 2016

(65) Prior Publication Data

US 2016/0151185 A1 Jun. 2, 2016

Related U.S. Application Data

(63) Continuation of application No. 13/797,636, filed on Mar. 12, 2013, now Pat. No. 9,283,101.

(51) Int. Cl.
*A61F 2/966* (2013.01)
*A61F 2/95* (2013.01)
*A61F 2/01* (2006.01)

(52) U.S. Cl.
CPC ............... *A61F 2/966* (2013.01); *A61F 2/95* (2013.01); *A61F 2002/011* (2013.01);
(Continued)

(58) Field of Classification Search
CPC .......... A61F 2/2436; A61F 2/95; A61F 2/962; A61F 2/966; A61F 2002/9517; A61F 2002/9665
See application file for complete search history.

(56) References Cited

U.S. PATENT DOCUMENTS 5,534,007 A   7/1996   St. Germain et al.
5,676,654 A   10/1997  Ellis et al.
(Continued)

FOREIGN PATENT DOCUMENTS

EP    1208816 A2      5/2002
JP    11-505162       5/1999
JP    2010-012251 A   1/2010

OTHER PUBLICATIONS

U.S. Appl. No. 15/163,984 (US 2016/0262920), filed May 25, 2015 (Sep. 15, 2016).

(Continued)

*Primary Examiner* — Ryan J. Severson
*Assistant Examiner* — Christian D Knauss
(74) *Attorney, Agent, or Firm* — Baker Botts L.L.P.

(57) ABSTRACT

Catheter including a pressure chamber defined by proximal and distal seals and inner and outer tubular members. An actuator member, moveable between first and second positions, is disposed within the pressure chamber. Fluid introduced into the pressure chamber applies a force on the actuator member to move the actuator member toward the second position. A lock mechanism, disposed between inner and outer tubular members, includes a latch having an engaged condition preventing movement of the outer tubular member relative the inner member and a disengaged condition allowing movement the outer member. The latch is shifted to the disengaged condition when the actuator member is moved to the second position. With the actuator member in the second position and the latch in the disengaged condition, fluid introduced through the fluid flow port and into the pressure chamber applies a force on the proximal seal to urge the outer tubular member proximally.

18 Claims, 12 Drawing Sheets

(52) U.S. Cl.
CPC ............... *A61F 2002/9517* (2013.01); *A61F 2250/0019* (2013.01); *A61F 2250/0021* (2013.01)

(56) References Cited

U.S. PATENT DOCUMENTS

| | | | |
|---|---|---|---|
| 5,695,468 | A | 12/1997 | Lafontaine et al. |
| 5,709,703 | A | 1/1998 | Lukic et al. |
| 5,776,141 | A | 7/1998 | Klein et al. |
| 5,817,101 | A | 10/1998 | Fiedler |
| 5,989,263 | A | 11/1999 | Shmulewitz |
| 6,056,759 | A | 5/2000 | Fiedler |
| 6,059,813 | A | 5/2000 | Vrba et al. |
| 6,113,608 | A | 9/2000 | Monroe et al. |
| 6,214,037 | B1 | 4/2001 | Mitchell et al. |
| 6,287,285 | B1 | 9/2001 | Michal et al. |
| 6,425,898 | B1 | 7/2002 | Wilson et al. |
| 6,514,261 | B1 | 2/2003 | Randall et al. |
| 6,520,983 | B1 | 2/2003 | Colgan et al. |
| 6,541,116 | B2 | 4/2003 | Michal et al. |
| 6,605,109 | B2 | 8/2003 | Fiedler |
| 6,884,257 | B1 | 4/2005 | Cox |
| 6,942,682 | B2 | 9/2005 | Vrba et al. |
| 6,945,989 | B1 | 9/2005 | Betelia et al. |
| 7,163,552 | B2 | 1/2007 | Diaz |
| 7,632,296 | B2 | 12/2009 | Malewicz |
| 7,740,652 | B2 | 6/2010 | Gerdts et al. |
| 7,799,065 | B2 | 9/2010 | Pappas |
| 7,875,067 | B2 | 1/2011 | Von Oepen et al. |
| 8,118,853 | B2 | 2/2012 | Grewe |
| 8,435,279 | B2 | 5/2013 | Beyerlein et al. |
| 8,652,198 | B2 | 2/2014 | Andreas et al. |
| 8,685,076 | B2 | 4/2014 | Gerdts et al. |
| 9,119,742 | B2 | 9/2015 | Chuter et al. |
| 9,283,101 | B2 | 3/2016 | Shumer et al. |
| 9,326,875 | B2 | 5/2016 | Shumer et al. |
| 2001/0027323 | A1 | 10/2001 | Roy, III et al. |
| 2001/0044630 | A1 | 11/2001 | Stack et al. |
| 2002/0009535 | A1 | 1/2002 | Michal et al. |
| 2002/0010420 | A1 | 1/2002 | Bagaoisan et al. |
| 2002/0026182 | A1 | 2/2002 | Joye et al. |
| 2002/0045929 | A1* | 4/2002 | Diaz .................. A61F 2/95 623/1.11 |
| 2002/0058951 | A1 | 5/2002 | Fiedler |
| 2002/0133118 | A1 | 9/2002 | Gerdts et al. |
| 2002/0165574 | A1 | 11/2002 | Ressemann et al. |
| 2003/0176910 | A1 | 9/2003 | Vrba et al. |
| 2003/0187474 | A1 | 10/2003 | Keegan et al. |
| 2004/0143315 | A1 | 7/2004 | Bruun et al. |
| 2004/0193178 | A1* | 9/2004 | Nikolchev ....... A61B 17/12022 606/108 |
| 2004/0193243 | A1 | 9/2004 | Mangiardi et al. |
| 2005/0149166 | A1 | 7/2005 | Schaeffer et al. |
| 2005/0209674 | A1 | 9/2005 | Kutscher et al. |
| 2005/0222557 | A1 | 10/2005 | Baxter et al. |
| 2006/0030923 | A1 | 2/2006 | Gunderson |
| 2006/0106366 | A1 | 5/2006 | Wang |
| 2006/0200191 | A1 | 9/2006 | Zadno-azizi |
| 2006/0200221 | A1 | 9/2006 | Malewicz |
| 2007/0078506 | A1 | 4/2007 | McCormick et al. |
| 2007/0083188 | A1 | 4/2007 | Grandt et al. |
| 2007/0100413 | A1 | 5/2007 | Dwyer et al. |
| 2007/0123971 | A1* | 5/2007 | Kennedy, II .............. A61F 2/95 623/1.11 |
| 2008/0118544 | A1 | 5/2008 | Wang |
| 2008/0125711 | A1 | 5/2008 | Alpini et al. |
| 2008/0294230 | A1* | 11/2008 | Parker ....................... A61F 2/95 623/1.11 |
| 2009/0018529 | A1 | 1/2009 | Hoffman et al. |
| 2009/0204197 | A1 | 8/2009 | Dorn et al. |
| 2009/0292262 | A1* | 11/2009 | Adams ................. A61F 2/2436 604/264 |
| 2009/0312832 | A1 | 12/2009 | Delap |
| 2010/0087906 | A1 | 4/2010 | Dorn et al. |
| 2010/0286756 | A1 | 11/2010 | Dorn et al. |
| 2011/0112567 | A1 | 5/2011 | Lenker et al. |
| 2011/0307049 | A1 | 12/2011 | Kao |
| 2012/0148175 | A1 | 6/2012 | Wesselmann |
| 2013/0073024 | A1 | 3/2013 | Russo et al. |
| 2013/0138090 | A1 | 5/2013 | Fargahi |
| 2013/0297011 | A1 | 11/2013 | Morris et al. |
| 2013/0304179 | A1 | 11/2013 | Bialas et al. |
| 2013/0304181 | A1 | 11/2013 | Green et al. |
| 2014/0194969 | A1 | 7/2014 | Headley |
| 2014/0214151 | A1 | 7/2014 | Ibeling |
| 2014/0277356 | A1 | 9/2014 | Shumer et al. |

OTHER PUBLICATIONS

U.S. Appl. No. 15/180,655 (US 2016/0287420), filed Jun. 13, 2013 (Oct. 6, 2016).
U.S. Appl. No. 13/467,679, Aug. 25, 2017 Notice of Abandonment.
U.S. Appl. No. 13/467,679, Apr. 24, 2017 Applicant Initiated Interview Summary.
U.S. Appl. No. 13/467,679, Feb. 9, 2017 Final Office Action.
U.S. Appl. No. 13/467,679, Nov. 22, 2016 Amendment and Request for Continued Examination (RCE).
U.S. Appl. No. 13/467,679, Aug. 22, 2016 Final Office Action.
U.S. Appl. No. 13/467,679, May 11, 2016 Response to Non-Final Office Action.
U.S. Appl. No. 13/467,679, Feb. 11, 2016 Non-Final Office Action.
U.S. Appl. No. 13/467,679, Oct. 14, 2014 Response to Restriction Requirement.
U.S. Appl. No. 13/801,588, Mar. 31, 2016 Issue Fee Payment.
U.S. Appl. No. 14/643,110, May 27, 2016 Issue Fee Payment.
U.S. Appl. No. 14/643,110, Feb. 29, 2016 Notice of Allowance.
U.S. Appl. No. 14/653,582, Nov. 14, 2017 Non-Final Office Action.
U.S. Appl. No. 14/653,582, Oct. 6, 2017 Response to Restriction Requirement.
U.S. Appl. No. 14/653,582, Aug. 14, 2017 Restriction Requirement.
U.S. Appl. No. 14/767,968, Nov. 30, 2017 Non-Final Office Action.
U.S. Appl. No. 15/180,655, Feb. 13, 2018 Notice of Allowance.
U.S. Appl. No. 15/180,655, Feb. 6, 2018 Notice of Allowance.
U.S. Appl. No. 15/180,655, Jan. 17, 2018 Notice of Allowance.
U.S. Appl. No. 15/180,655, Sep. 5, 2017 Response to Non-Final Office Action.
U.S. Appl. No. 15/180,655, May 2, 2017 Non-Final Office Action.
U.S. Appl. No. 13/467,660 (U.S. Pat. No. 9,011,513), filed May 9, 2012 (Apr. 21, 2015).
U.S. Appl. No. 13/467,679 (US 2013/0304180), filed May 9, 2012 (Nov. 14, 2013).
U.S. Appl. No. 13/467,715 (US 2013/0304181), filed May 9, 2012 (Nov. 14, 2013).
U.S. Appl. No. 13/797,636 (US 2014/0277356), filed Mar. 12, 2013 (Sep. 18, 2014).
U.S. Appl. No. 13/801,588 (US 2014/0276412), filed Mar. 13, 2013 (Sep. 18, 2014).
U.S. Appl. No. 14/643,110 (US 2015/0245937), filed Mar. 10, 2015 (Sep. 3, 2015).
U.S. Appl. No. 14/653,582, filed Jun. 18, 2015.
U.S. Appl. No. 14/767,968, filed Aug. 14, 2015.
U.S. Appl. No. 13/467,660, Oct. 7, 2013 Non-Final Office Action.
U.S. Appl. No. 13/467,660, Jan. 7, 2014 Response to Non-Final Office Action.
U.S. Appl. No. 13/467,660, Jul. 17, 2014 Final Office Action.
U.S. Appl. No. 13/467,660, Oct. 14, 2014 Response after Final Action.
U.S. Appl. No. 13/467,660, Nov. 25, 2014 Notice of Allowance.
U.S. Appl. No. 13/467,660, Feb. 25, 2015 Issue Fee Payment.
U.S. Appl. No. 13/467,679, Aug. 22, 2014 Restriction Requirement.
U.S. Appl. No. 13/467,715, Jan. 20, 2016 Issue Fee Payment.
U.S. Appl. No. 13/467,715, Dec. 18, 2015 Notice of Allowance.
U.S. Appl. No. 13/467,715, Sep. 9, 2015 Restriction Requirement.
U.S. Appl. No. 13/797,636, Feb. 5, 2016 Issue Fee Payment.
U.S. Appl. No. 13/797,636, Dec. 10, 2015 Notice of Allowance.
U.S. Appl. No. 13/797,636, Oct. 30, 2015 Response to Non-Final Office Action.
U.S. Appl. No. 13/797,636, Jun. 30, 2015 Non-Final Office Action.

(56) References Cited

OTHER PUBLICATIONS

U.S. Appl. No. 13/801,588, Feb. 1, 2016 Notice of Allowance.
U.S. Appl. No. 13/801,588, Jan. 22, 2016 Applicant Initiated Interview Summary.
U.S. Appl. No. 13/801,588, Nov. 19, 2015 Response to Non-Final Office Action.
U.S. Appl. No. 13/801,588, Aug. 20, 2015 Non-Final Office Action.
U.S. Appl. No. 13/801,588, Jul. 9, 2015 Restriction Requirement Filed.
U.S. Appl. No. 14/643,110, Oct. 30, 2015 Response to Non-Final Office Action.
U.S. Appl. No. 14/643,110, Jul. 30, 2015 Non-Final Office Action.
U.S. Appl. No. 14/767,968, Dec. 10, 2015 Notice of Allowance.
CN Office Action dated Jun. 30, 2015 in CN Patent Application No. 201380007953.4 (with English translation).
International Search Report and Written Opinion for PCT/US2013/036881, dated Aug. 2, 2013.
International Search Report and Written Opinion for PCT/US2013/036884, dated Aug. 2, 2013.
International Search Report and Written Opinion for PCT/US2013/030513, dated Aug. 2, 2013.
International Search Report and Written Opinion for PCT/US2013/069477, dated Jan. 8, 2014.
International Search Report for PCT/US2013/030830, dated Jan. 15, 2014.
International Search Report for PCT/US2013/068306, dated Jan. 8, 2014.
U.S. Appl. No. 15/163,984, Jun. 22, 2018 Non-Final Office Action.
U.S. Appl. No. 15/163,984, dated Feb. 15, 2019, Final Office Action.

\* cited by examiner

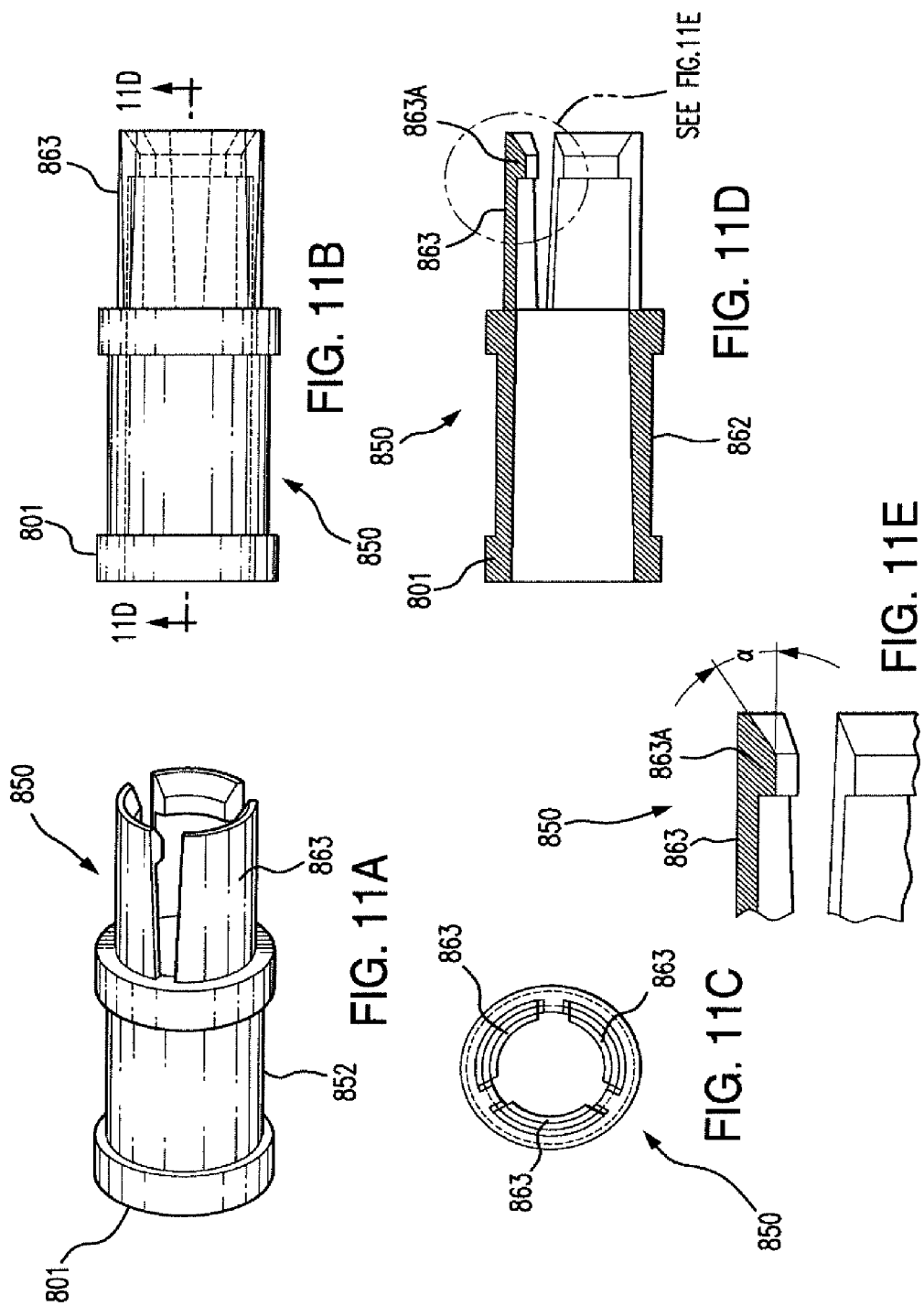

CATHETER HAVING HYDRAULIC ACTUATOR AND LOCKING SYSTEM

CROSS-REFERENCE TO RELATED APPLICATIONS

This application claims priority to and is a continuation of U.S. application Ser. No. 13/797,636 filed Mar. 12, 2013, which is incorporated by reference herein in its entirety.

BACKGROUND OF THE DISCLOSED SUBJECT MATTER

Field of the Disclosed Subject Matter

The disclosed subject matter relates to catheters used in the delivery of medical devices such as self-expanding stents for treating the luminal systems of a patient. Specifically, the disclosed subject matter relates to a delivery catheter having a retractable sheath moved by a hydraulic actuator.

Description of the Related Art

A variety of systems using a retractable sheath are known for intraluminal delivery of a medical device, such as a stent or filter. However, there remains a need for continued improvement of such known delivery systems.

An example of such a system is described in U.S. Pat. No. 6,425,898 to Wilson et al., which is incorporated by reference herein, wherein a delivery system is provided having an inner member with a stop attached to the inner member. During deployment, the stop prevents the stent from migrating proximally during retraction of the sheath for stent deployment.

Conventional self-expanding stent delivery systems generally comprise a handle portion and an elongated shaft, wherein the stent is disposed within a delivery portion at the distal end of the shaft. To deploy the stent, an outer sheath is provided which can be retracted relative to the stent to release the stent from its delivery configuration. The sheath in such systems generally spans the full length of the catheter resulting in an increased profile and stiffness over the entire length of the catheter. Such stiffness and increased profile at the distal end of the catheter can restrict certain applications, such as neuro and other indications of particular size limitations. Further, because the sheath spans the full length of the catheter there is an increased risk of the sheath binding with other components of the catheter during passage through the tortuous luminal system of a patient, thus inhibiting the deployment of the stent.

Another issue with such delivery systems is that the sheath is generally pulled back in a 1-to-1 ratio with the user's input (force). Because the stent may embed in the outer sheath during storage and shipping, and due to larger static friction forces, a large amount of initial input is typically required to release the stent which may lead to incorrect placement. When initially releasing the stent, it may be desirable to slowly pull back the sheath for proper placement and then more readily retract the sheath to prevent inadvertent movement of the stent.

Further, the amount of force that is required to retract the sheath, particularly for stents of greater length as required for peripheral indications, can be substantial. To overcome this issue, a lubricious liner can be used to decrease the amount of force required to retract the sheath. However, there remains a need for an improved delivery system for self-expanding stents having reduced force requirements for delivery of a self-expanding stent or the like.

There thus remains a continued need for an efficient and economic system for delivering a medical device that is easy to use and provides accurate placement. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes a catheter comprising, among other things, an inner tubular member having a proximal end portion, a distal end portion and an exterior surface, the inner tubular member further having a fluid lumen defined therein, the fluid lumen having a fluid flow port defined by the exterior surface along the distal end portion of the inner tubular member. The catheter further includes an outer tubular member movable relative to the inner tubular member, the outer tubular member having a proximal end, a distal end and an interior surface directed toward the exterior surface of the inner tubular member. A proximal seal extends from the interior surface of the outer tubular member toward the exterior surface of the inner tubular member. The proximal seal is located proximal to the fluid flow port. A distal seal extends from the exterior surface of the inner tubular member toward the interior surface of the outer tubular member. The distal seal is located distal to the fluid flow port. A pressure chamber is defined by the proximal seal, the distal seal, the exterior surface of the inner tubular member, and interior surface of the outer tubular member.

An actuator member is disposed within the pressure chamber, the actuator member having a seal section and a cam section. The actuator member is moveable between a first position and a second position. Fluid introduced through the fluid flow port and into the pressure chamber applies a force on the seal section to move the actuator member from the first position toward the second position. Additionally, a lock mechanism is disposed between the exterior surface of the inner tubular member and interior surface of the outer tubular member. The lock mechanism includes a latch having an engaged condition to prevent movement of the outer tubular member relative the inner tubular member and a disengaged condition to allow movement the outer tubular member relative the inner tubular member. The latch is shifted to the disengaged condition by the cam section when the actuator member is moved to the second position. With the actuator member in the second position and the latch in the disengaged condition, fluid introduced through the fluid flow port and into the pressure chamber applies a force on the proximal seal to urge the outer tubular member in a proximal direction.

In accordance with another aspect of the disclosed subject matter, a method of deploying a catheter is provided, comprising, among other things, providing a catheter as described above. Particularly, the catheter includes an inner tubular member having a proximal end portion, a distal end portion and an exterior surface. The inner tubular member has a fluid lumen defined therein, the fluid lumen having a fluid flow port defined by the exterior surface along the distal end portion of the inner tubular member. An outer tubular member movable relative to the inner tubular member is provided, the outer tubular member having a proximal end, a distal end and an interior surface directed toward the exterior surface of the inner tubular member. The catheter further includes a proximal seal extending from the interior surface of the outer tubular member toward the exterior surface of the inner tubular member, the proximal seal located proximal to the fluid flow port. A distal seal extending from the exterior surface of the inner tubular member toward the interior surface of the outer tubular member is provided, the distal seal located distal to the fluid flow port. A pressure chamber is thereby provided defined by the proximal seal, the distal seal, the exterior surface of the inner tubular member, and interior surface of the outer tubular member.

Further in accordance with the method herein, the catheter includes an actuator member disposed within the pressure chamber, wherein the actuator member has a seal section and a cam section. The actuator member is moveable between a first position and a second position. Fluid introduced through the fluid flow port and into the pressure chamber applies a force on the seal section to move the actuator member from the first position toward the second position. A lock mechanism disposed between the exterior surface of the inner tubular member and interior surface of the outer tubular member. The lock mechanism includes a latch having an engaged condition to prevent movement of the outer tubular member relative the inner tubular member and a disengaged condition to allow movement the outer tubular member relative the inner tubular member. The latch is shifted to the disengaged condition by the cam section when the actuator member is moved to the second position.

Using the catheter as described above, the method further includes disposing a device between the exterior surface of the inner tubular member and the interior surface of the outer tubular member at a location distal to the distal seal. The method further includes introducing fluid through the fluid flow port and into the pressure chamber to move the actuator member toward the second position and shift the latch of the lock mechanism to the disengaged condition, wherein, with the actuator member in the second position and the latch in the disengaged condition, fluid introduced through the fluid flow port and into the pressure chamber applies a force on the proximal seal to urge the outer tubular member in a proximal direction.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 6 is a cross sectional side view of the distal end section of an alternative embodiment of a catheter in accordance with the disclosed subject matter with the sheath in a fully retracted position.

FIG. 6A is a cross sectional view of the catheter of FIG. 6 taken at line 6a-6a.

FIG. 11A is a perspective view of a locking mechanism, FIG. 11B is a side view of the lock mechanism of FIG. 11A, FIG. 11C is a front view of the lock mechanism of FIG. 11A, FIG. 11D is a cross section of the lock mechanism of FIG. 11B across lines 11D-11D, and FIG. 11E is a detail view of the lock mechanism of FIG. 11D about line 11E, in accordance with the disclosed subject matter.

DETAILED DESCRIPTION

Figure 1:
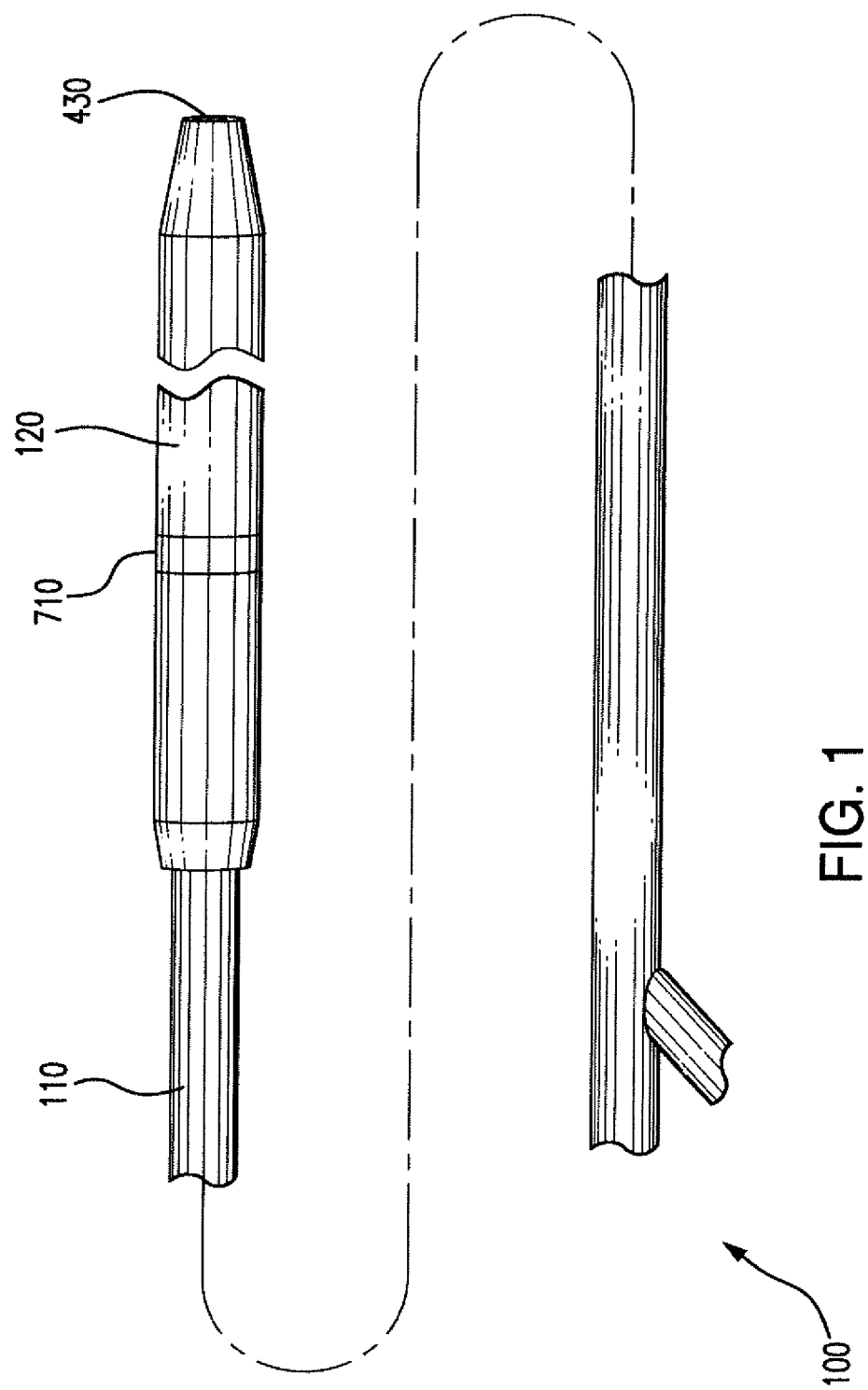
FIG. 1 is a schematic side view of a representative catheter in accordance with the disclosed subject matter.

Reference will now be made in detail to embodiments of the disclosed subject matter, an example of which is illustrated in the accompanying drawings. The disclosed subject matter will be described in conjunction with the detailed description of the system.

As disclosed herein, the devices presented herein can be used for treating the luminal system of a patient. In particular, the disclosed subject matter is particularly suited for treatment of the cardiovascular system and the peripheral system of a patient.

In accordance with the disclosed subject matter, a catheter is provided comprising, among other things, an inner tubular member having a proximal end portion, a distal end portion and an exterior surface, the inner tubular member further having a fluid lumen defined therein, the fluid lumen having a fluid flow port defined by the exterior surface along the distal end portion of the inner tubular member. The catheter further includes an outer tubular member movable relative to the inner tubular member, the outer tubular member having a proximal end, a distal end and an interior surface directed toward the exterior surface of the inner tubular member. A proximal seal extends from the interior surface of the outer tubular member toward the exterior surface of the inner tubular member. The proximal seal is located proximal to the fluid flow port. A distal seal extends from the exterior surface of the inner tubular member toward the interior surface of the outer tubular member. The distal seal is located distal to the fluid flow port. A pressure chamber is defined by the proximal seal, the distal seal, the exterior surface of the inner tubular member, and interior surface of the outer tubular member.

An actuator member is disposed within the pressure chamber, the actuator member having a seal section and a cam section. The actuator member is moveable between a first position and a second position. Fluid introduced through the fluid flow port and into the pressure chamber applies a force on the seal section to move the actuator member from the first position toward the second position. Additionally, a lock mechanism is disposed between the exterior surface of the inner tubular member and interior surface of the outer tubular member. The lock mechanism includes a latch having an engaged condition to prevent movement of the outer tubular member relative the inner tubular member and a disengaged condition to allow movement the outer tubular member relative the inner tubular member. The latch is shifted to the disengaged condition by the cam section when the actuator member is moved to the second position. With the actuator member in the second position and the latch in the disengaged condition, fluid introduced through the fluid flow port and into the pressure chamber applies a force on the proximal seal to urge the outer tubular member in a proximal direction.

A method for deploying the catheter described above is also disclosed. The details of the method in deployment will be described in detail in conjunction with the features of the catheter.

Figure 2:
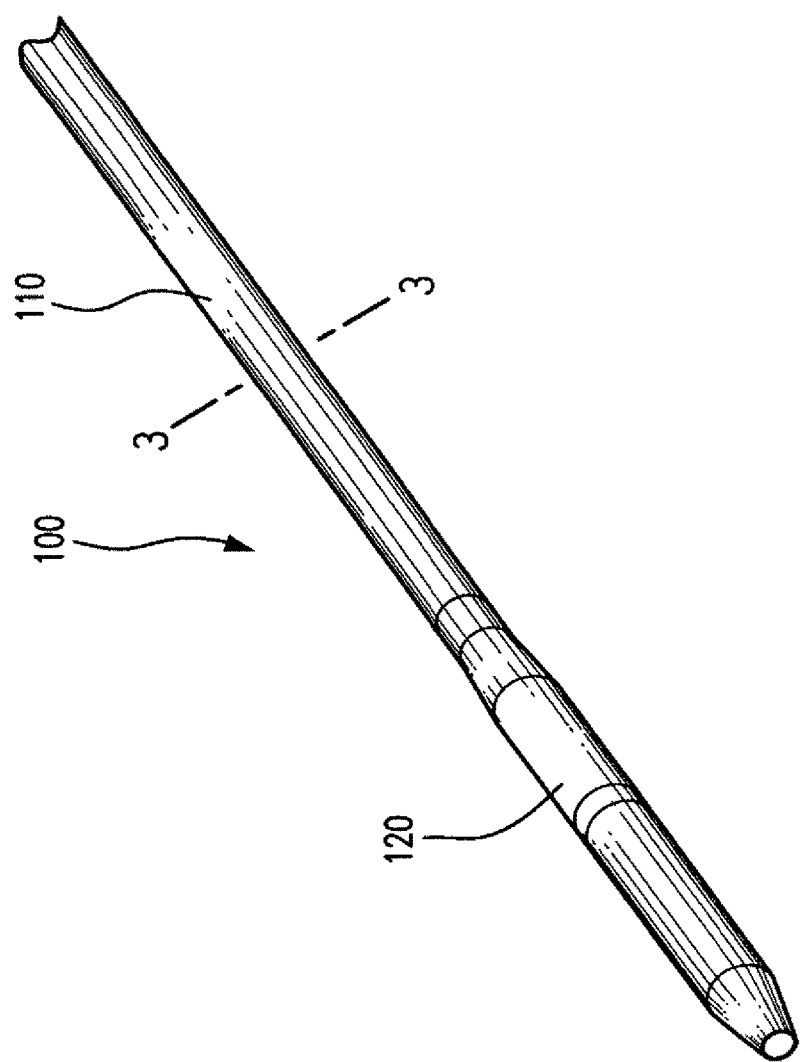
FIG. 2 is a perspective view of the distal end section of the catheter of FIG. 1.

Solely for purpose of illustration, an exemplary embodiment of a hydraulic delivery system for a self-expanding stent or the like, at least a portion of which is delivered within a vasculature, is shown schematically in FIGS. 1 and 2. The examples herein are not intended to limit the scope of the disclosed subject matter in any manner. Particularly, and as illustrated, the hydraulic delivery system embodied herein is a catheter 100 for cardiovascular intervention or the like. Catheters for other uses and indications, such as peripheral and below-the-knee interventions, are contemplated herein. The catheter 100 includes an inner tubular member 110 having a proximal end portion, a distal end portion, and an exterior surface. The catheter 100 further includes an outer tubular member or sheath 120 which is movable relative to the inner tubular member 110 and has a proximal end, a distal end and an interior surface directed toward the exterior surface of the inner tubular member 110. As shown in FIG. 2, the outer tubular member 120 is disposed only at a distal end portion of the catheter in this embodiment. For other embodiments, the outer tubular member 120 can be disposed at the proximal end portion and/or the distal end portion of the catheter. As described further herein, the catheter of the disclosed subject matter can be configured to deliver a medical device, such as a stent, of any suitable length. That is, the catheter can be configured to generate a force sufficient to retract the outer tubular member, wherein the generated force is greater than the resistance force caused by the medical device acting on the outer tubular member.

Figure 3A:
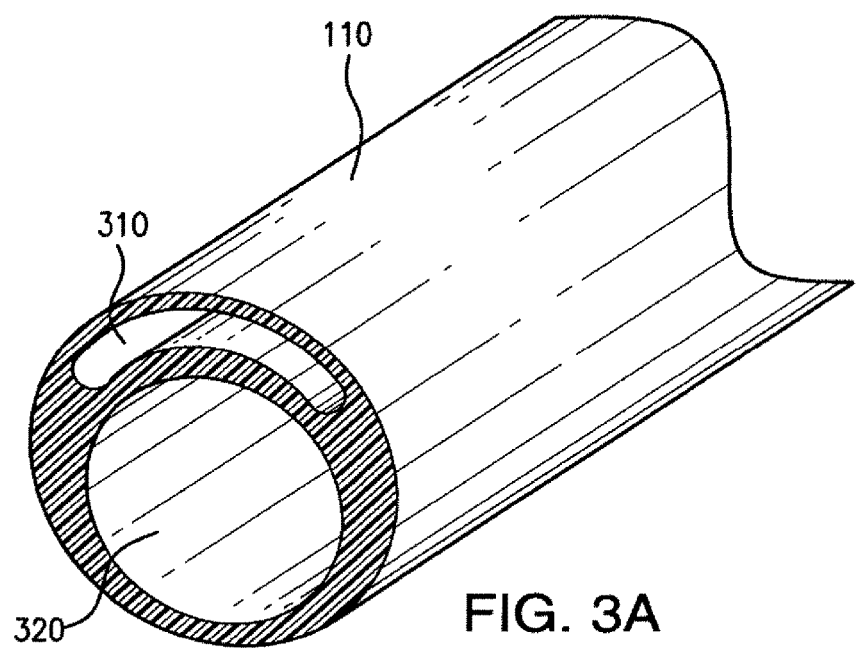
FIG. 3A is a cross sectional perspective view of the catheter of FIG. 2 taken along line 3-3.

Solely for purpose of illustration, reference is made to FIG. 3A which depicts a representative cross sectional view of an exemplary inner tubular member 110 along lines 3-3 of FIG. 2, in accordance with the disclosed subject matter. The inner tubular member 110 further has a fluid lumen 310 defined therein. In one embodiment the inner tubular member can also have a guidewire lumen 320 defined at least along a length therein. For example, the guidewire lumen 320, if provided, can extend over the entire length of the inner tubular member 110 such as for an "over-the-wire" configuration, or only along a distal length such as for a "rapid exchange" embodiment. Alternatively the catheter 100 can have a single-lumen design and the guidewire and pressurized fluid can share the same lumen (not shown), wherein a seal or valve can be provided at distal and proximal ends.

Figure 3B:
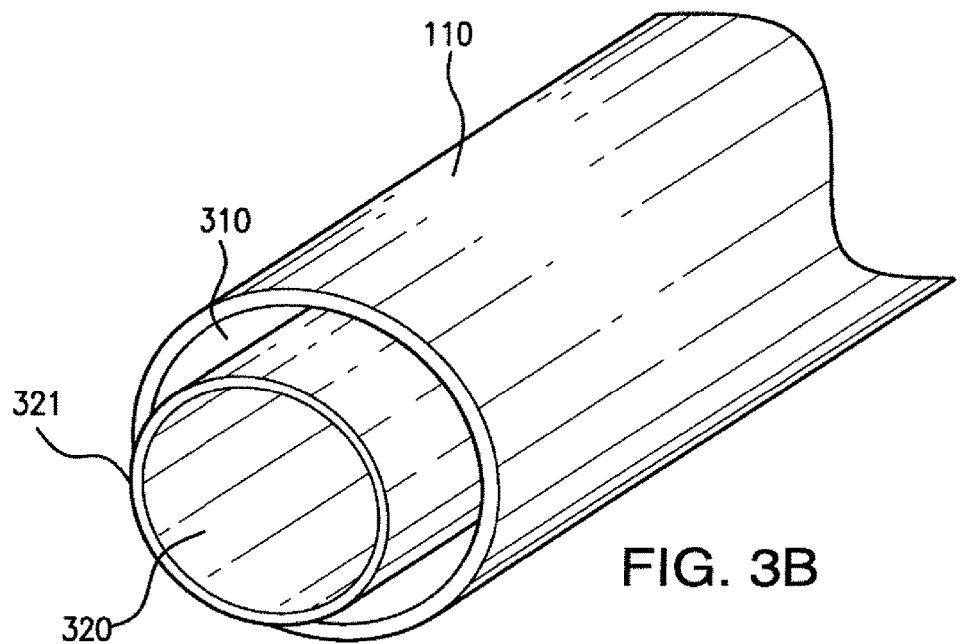
FIG. 3B is a cross sectional perspective view of another embodiment the catheter of FIG. 2 taken along line 3-3.

FIG. 3B depicts another embodiment of a representative cross sectional view of an exemplary inner tubular member 110 along lines 3-3 of FIG. 2. In this embodiment, as shown in FIG. 3B solely for purposes of illustration, the guidewire lumen 320 can be defined at least in part by a separate guidewire tube 321 disposed within a fluid lumen 310 and sealed at either side, such as for example, by a marker (not shown). Such coaxial configurations allow for reduced diameter of the inner tubular member 110, and thus reduced profile. Indeed the guidewire tube 321 defining the guidewire lumen 320 can be formed by a thin membrane of suitable strength to prevent the guidewire from penetrating therethrough. Hydraulic fluid can thus flow within the fluid lumen 310 but outside the guidewire lumen 320.

Figure 4:
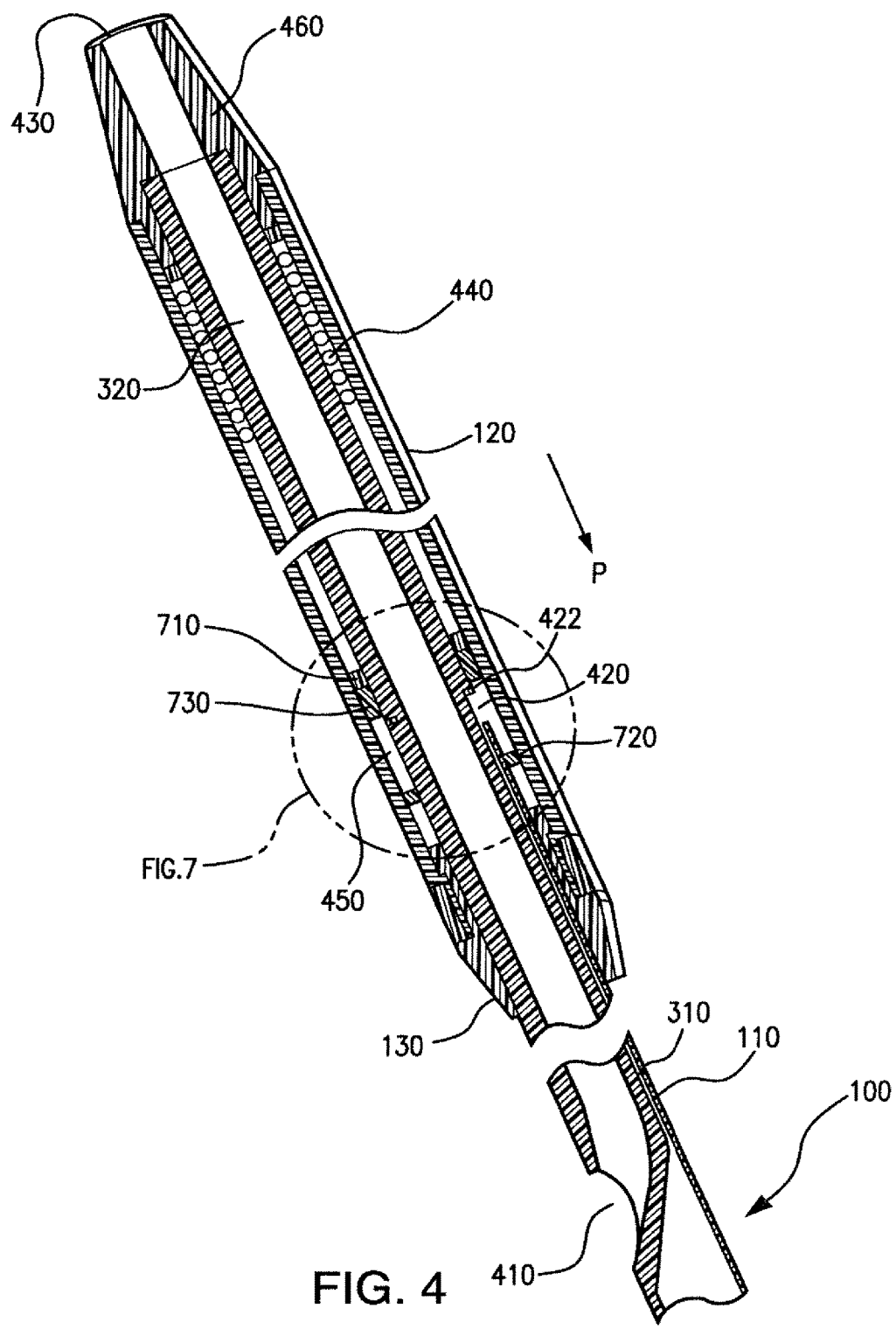
FIG. 4 is a cross sectional perspective view of the distal end section of a catheter in accordance with the disclosed subject matter with the sheath in a closed position.

Solely for purpose of illustration, reference is now made to a rapid exchange configuration of the catheter disclosed herein as shown in FIG. 4. Generally, the catheter includes an inner tubular member 110 having a proximal end portion, a distal end portion and an exterior surface. The inner tubular member 110 further includes a fluid lumen 310 having a fluid flow port 420 defined by the exterior surface 111 along a distal end portion of inner tubular member 110. The catheter further includes an outer tubular member 120 movable relative to the inner tubular member 110 and having a proximal end, a distal end and an interior surface 121 directed toward the exterior surface 111 of the inner tubular member 110. As described in more detail below, the fluid flow port 420 allows fluid to pass from within fluid lumen 310 into the space defined by the inner tubular member 110 and outer tubular member 120 for operation and retraction of the outer tubular member 120. A marker 422 can define the distal end of the fluid flow port 420. As embodied herein, the rapid exchange catheter further includes guidewire lumen 320 extending along a distal end portion of the catheter and including a proximal guidewire port 410 and a distal guidewire port 430.

Figure 5:
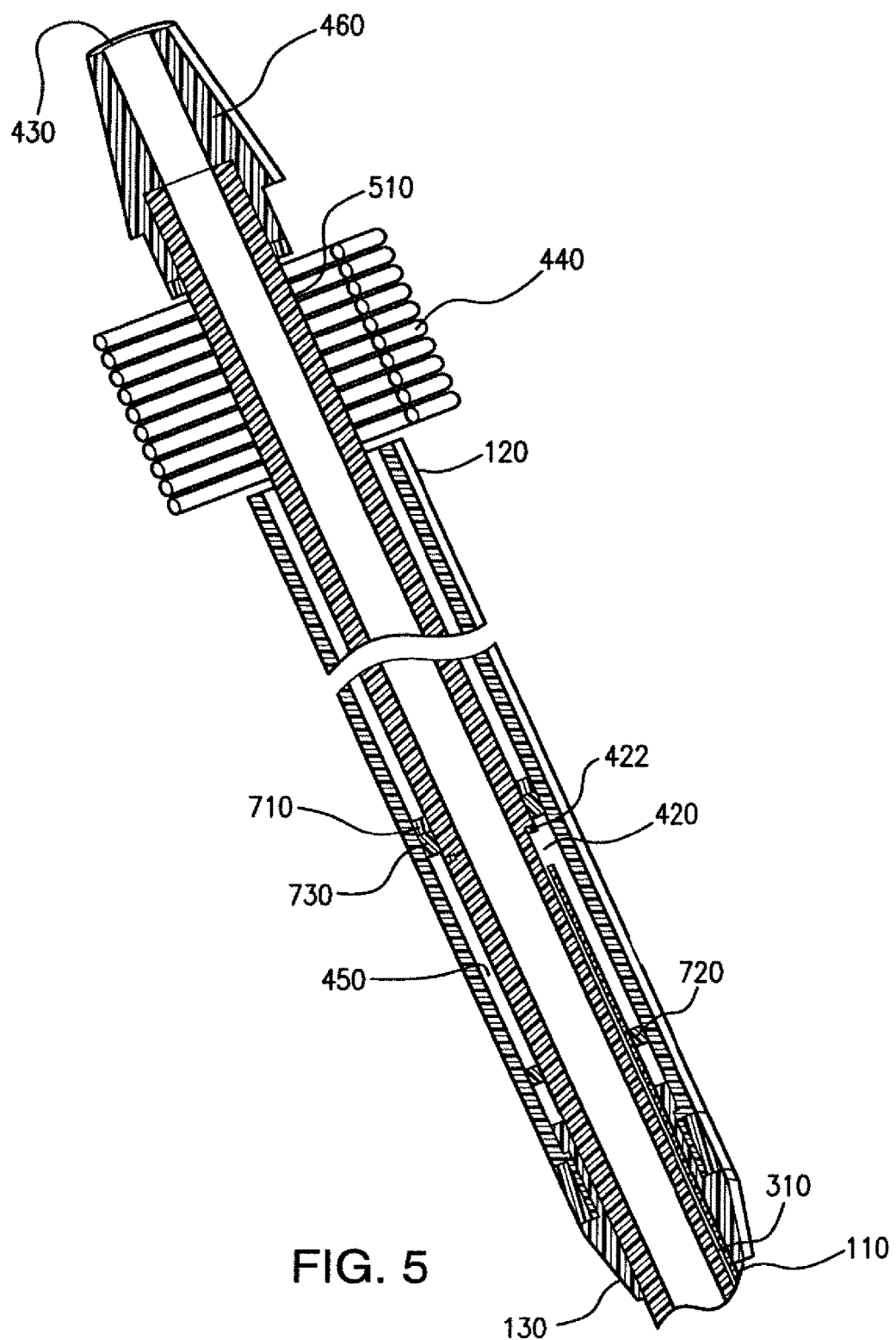
FIG. 5 is a cross sectional side view of the distal end of the catheter of FIG. 4 with the sheath in a fully retracted position.
Figures 6, 6A:
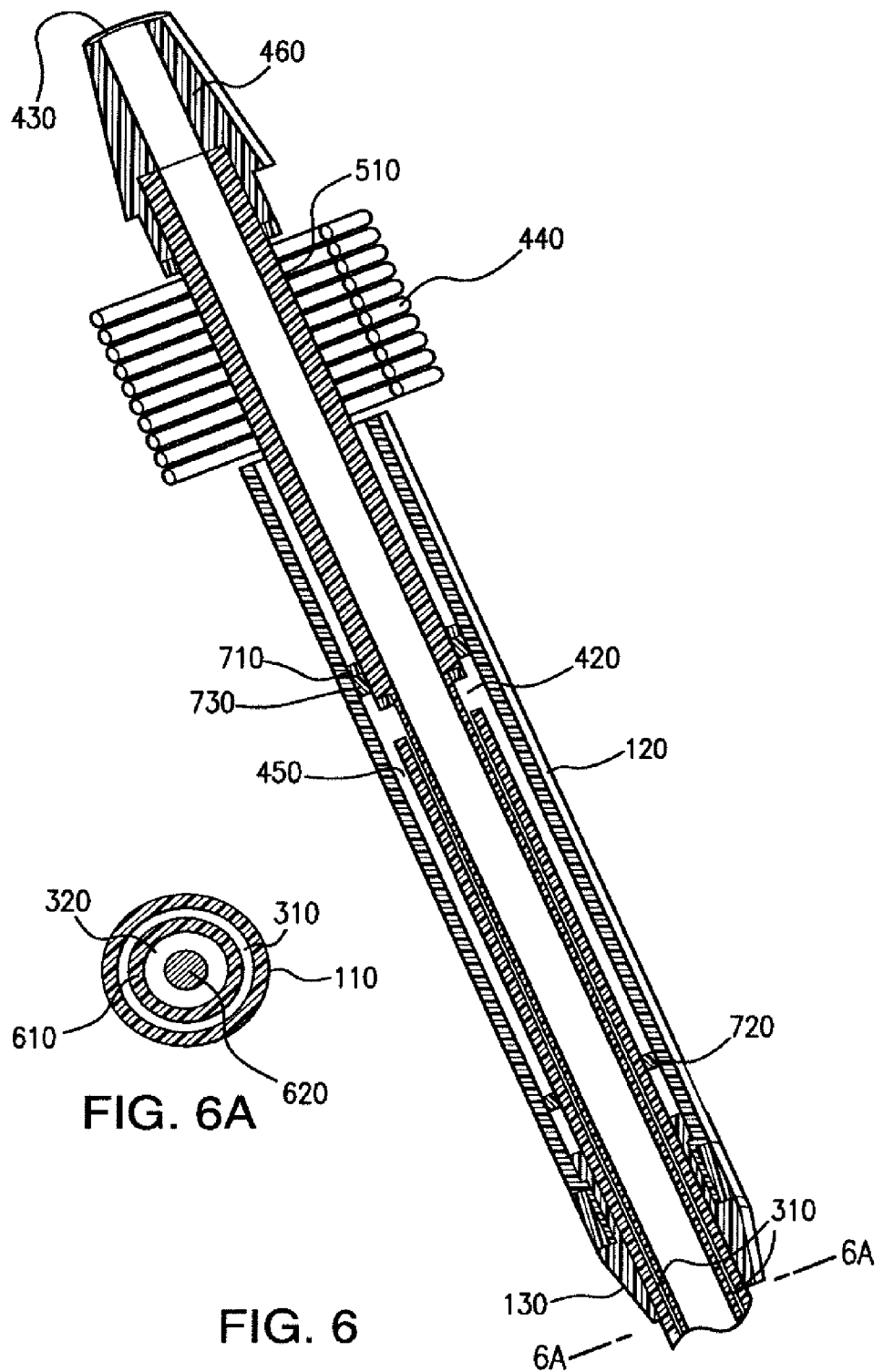

As illustrated, the outer tubular member 120 can be moved from an extended position as shown in FIG. 4 to a retracted position shown in FIG. 5. When extended, the outer tubular member 120 retains a medical device, such as a stent 440 as depicted herein, in a compressed or delivery condition. A distal tip 460 can also be provided to further enclose the medical device during delivery. When the outer tubular member 120 is retracted (as shown in FIGS. 5 and 6), the medical device is unsheathed and allowed to expand to a deployed condition.

The outer tubular member 120 can further include at least one movable tubular structure 130 coupled to the proximal end of the outer tubular member and/or the distal end of the outer tubular member. Further details about the movable tubular structure are set forth in the currently pending application entitled, "Catheter Having Movable Tubular Structure", assigned to Abbott Cardiovascular Systems Inc. and filed on the same day as the present application, the contents of which are incorporated by reference herein in its entirety.

The fluid lumen 310 has a fluid flow port 420. The fluid flow port 420 is defined with the exterior surface of the inner tubular member 110 along the inner tubular member 110. As described in more detail below, the fluid flow port 420 allows fluid to pass from within fluid lumen 310 into the space defined by the inner tubular member 110 and outer tubular member 120 and between the proximal seal 720 and the distal seal 730. A marker 422 can define the distal end of the fluid flow port 420.

Figure 7:
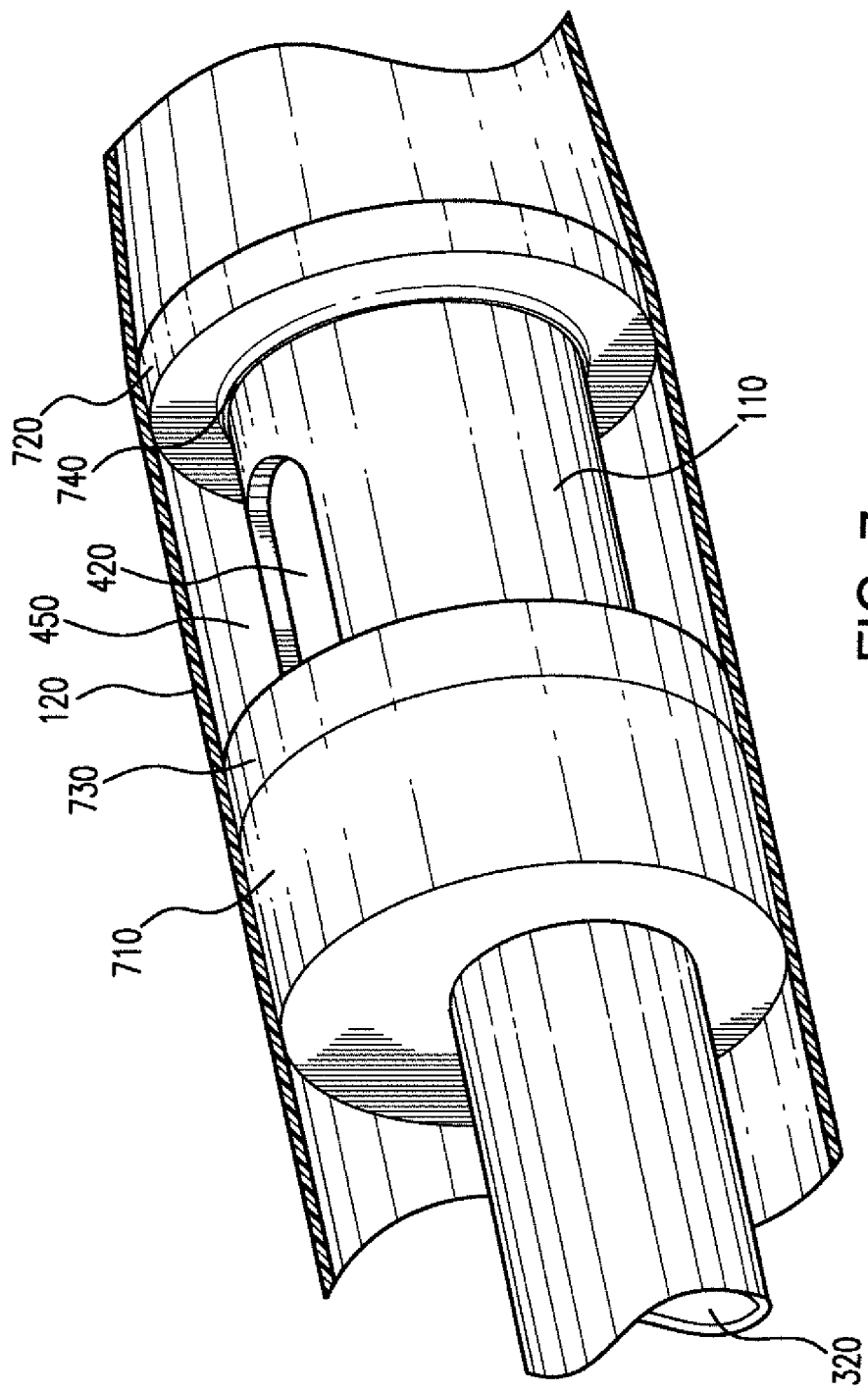
FIG. 7 is a detail perspective view of the catheter of FIG. 4 along line 7-7.
Figure 8:
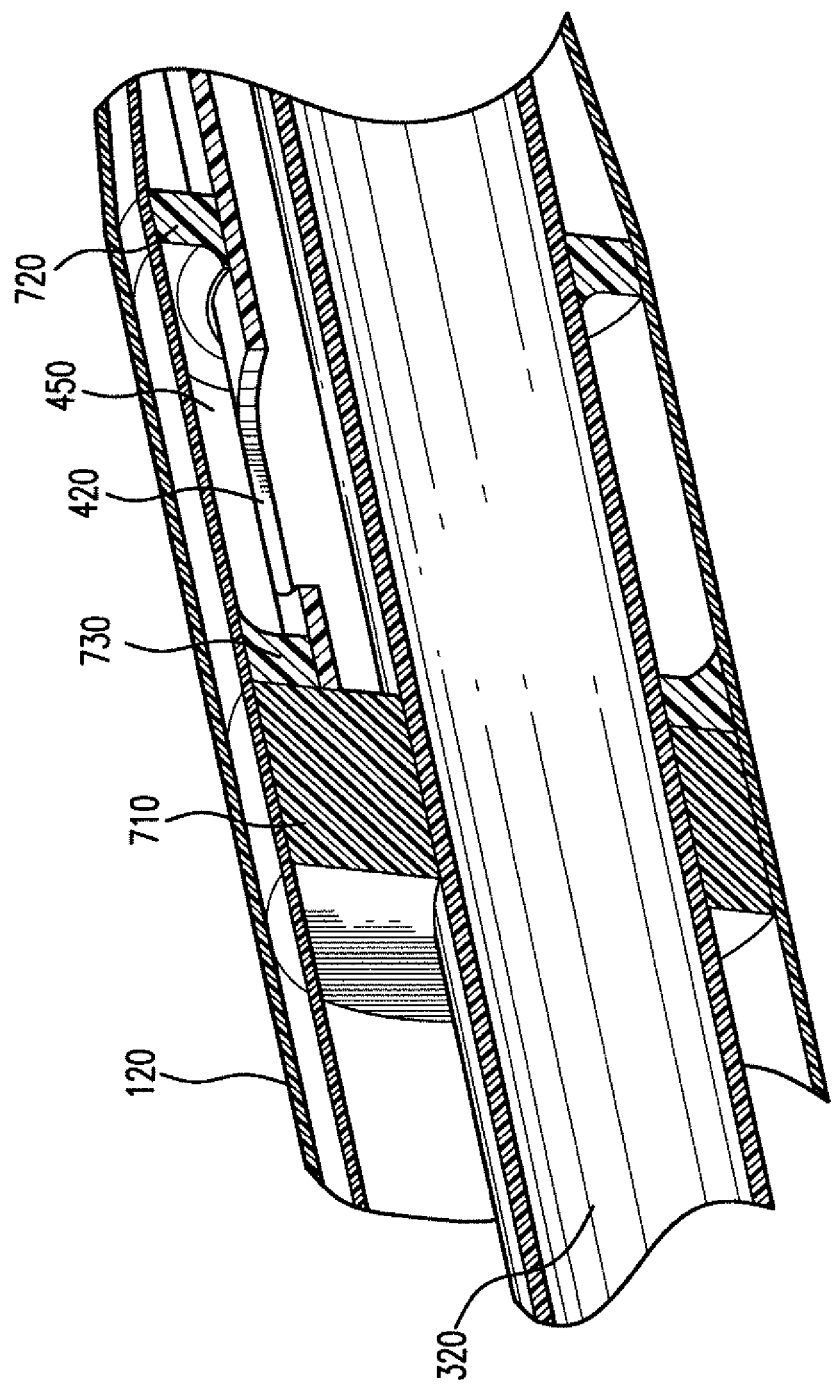
FIG. 8 is a cross sectional perspective view of the catheter of FIG. 7.

Solely for purpose of illustration, FIGS. 7 and 8 depict the pressure chamber 450, the proximal seal 720, and the distal seal 730. For purposes of discussion and illustration, other components within the pressure chamber are not illustrated herein, but can be understood from the more detailed description under U.S. application Ser. No. 13/467,679, entitled "Catheter having Dual Balloon Hydraulic Actuator" by Michael Green and Michael Bialas and owned by Abbott Cardiovascular Systems Inc.; and U.S. application Ser. No. 13/467,715, entitled "Catheter having Hydraulic Actuator with Tandem Chambers" by Michael Green and Michael Bialas, the contents of which are herein incorporated by reference in their entirety. The proximal seal 720 extends from the interior surface of the outer tubular member 120 toward the exterior surface of the inner tubular member 110 and is located proximal to fluid flow port 420. The proximal seal 720 is fixed to the interior surface of the outer tubular member 120 and moves freely relative to the inner tubular member 110.

With continued reference to FIGS. 7 and 8, catheter 100 also includes distal seal 730 spaced from the proximal seal 720. The distal seal 730 extends from the exterior surface of the inner tubular member 110 toward the interior surface of the outer tubular member 120 and is located distal to fluid flow port 420. The distal seal 730 is fixed to the exterior surface of the inner tubular member 110 and moves freely relative to the interior surface of the outer tubular member 120. In this manner, the outer tubular member 120 moves freely relative to the distal seal 730. As embodied herein, and as shown in FIG. 7, one or both of the proximal and distal seal can form a wiper seal 740 across the corresponding surface.

As shown in FIGS. 7 and 8, solely for purpose of illustration, the catheter 100 includes the pressure chamber 450 defined by the proximal seal 720, distal seal 730, the exterior surface 111 of the inner tubular member 110, and the interior surface 121 of the outer tubular member 120. Pressure chamber 450 is in fluid communication with fluid flow port 420.

As recognized in the art, the outer tubular member 120 constrains the medical device to be delivered. The medical device, e.g., a self expanding stent, is deployed by retracting the outer tubular member 120 (catheter sheath). Retraction is achieved by the introduction of fluid under pressure through the fluid lumen 310 using a conventional device, such as an indeflator or a syringe. The indeflator can include a threaded engagement or other locking mechanism to control pressurization and depressurization of the pressure chamber (not shown). Additionally, a pressure gauge can be provided with the indeflator to monitor the pressure system of the catheter. The indeflator can be configured to allow for the rapid release of hydraulic pressure to stop or inhibit the deployment of the stent. The indeflator can also be configured to create and/or maintain negative pressure in the catheter. The indeflator can further create a vacuum that decreases the profile of the catheter. For example, by creating a vacuum, the outer tubular member 120 disclosed herein can be configured to decrease in profile and/or lock in position. An example of a suitable indeflator is an Atrion indeflator Atrion Medical—55ATM.

An adapter can be provided at the proximal end of the catheter for access to the fluid lumen and can be configured for connecting to a fluid source (not shown). With reference to FIG. 7, fluid is introduced into the fluid lumen and exits the fluid lumen at flow port 420 and fills pressure chamber 450. Once sufficient fluid is introduced into the pressure chamber 450, a force is applied on the distal and proximal seals. Because the distal seal 730 is fixed relative to the inner member, only the proximal seal 720 and outer tubular member 120 attached thereto is capable of movement relative to the inner member in the proximal direction P. Movement of the proximal seal 720 upon the application of force in the pressure chamber 450 moves the outer tubular member 120 in the proximal direction P along the inner tubular member thereby allowing the medical device to be deployed. Distal seal 730, as embodied herein, is configured as a wiper-seal with the interior surface of outer tubular member 120. The outer tubular member 120 thus moves relative to distal seal 730. Proximal seal 720 mounted to the interior surface of outer tubular member 120 is configured as a wiper-seal with the exterior surface 111 of inner tubular member 110. The proximal seal 720 is free to move relative to the inner tubular member 110.

Although shown as a single piece seal construction in FIGS. 7 and 8, each seal of the disclosed subject matter can be a multi-piece seal assembly, if desired. For example, the seal assembly can include a seal member and a bushing to provide a backing to the seal member, as known in the art. The seals 720 and 730 can further be supported by proximal and distal bushings, respectively (not shown). In accordance with an aspect of the disclosed subject matter, the bushings can be constructed of any suitable material, including, but not limited to, PEEK, Pebax, HDPE, LDPE, a mixture of HDPE and LDPE, a Nylon blend such as L75/L25, or the like. Furthermore, the bushings can comprise a metallic material, combination low density polyethelene, silicon, nitril, soft Pebax 30, or other blends of suitable material, and can be coated with a suitable material as known in the art, and can include a coating.

As relatively high fluid pressures are needed to retract outer tubular member 120, the pressure chamber is formed to withstand such pressures with minimal to no leaks. A variety of suitable seal constructions and materials can be used, such as, but not limited to, sliding seals, rings, cups seals, lips seals, and compressed bushings. For example, each seal can be formed as a separate member and attached to the corresponding tube member, or can be formed as part of the tubular member. Solely for purposes of illustration, a hydrophilic material, such as, but not limited to, HydroMed™, Hydrothane™, Hydak™, can be used for the seals. Seals made of such material can be configured to swell when exposed to an aqueous environment, thus sealing more tightly while maintaining lubricity. The seals thus can comprise an expandable material or composite of materials to increase accordingly to match the dimensions of the outer tubular member. That is, the seal can be configured to expand with the outer tubular member to maintain an adequate seal.

As the pressure chamber expands, the exposed surface area of the seal can also increase, resulting in a proportional increase in retraction force at a given fluid pressure. Thus, an expanding pressure chamber provides for greater retraction force at a given pressure. Seals made of such material can be configured to swell when exposed to an aqueous environment, thus sealing more tightly while maintaining lubricity. Alternatively, the proximal and distal seals can be coated with a hydrophobic layer such as oil or wax or made of hydrophobic material such as a fluorocarbon or olefins like polypropylene to be used with a suitable pressurized fluid, to prevent swelling of the seals. Solely for example, silicone seals can be provided with a Hydromer 2314-172 coating. In another embodiment, O-rings can be used for the seal constructions comprised of silicone, buna, or other suitable elastomers. Furthermore, solely for purpose of example, the seal can include soft tubing such as a low durometer Pebax. Additionally or alternatively, a high viscosity hydraulic fluid can be used to inhibit leaks.

Embodiments of the disclosed subject matter allow the pressure chamber to operate with a variety of different suitable pressures. Solely for purpose of example, in one embodiment the pressure chamber can handle a positive pressure of up to 750 psi, and a negative pressure of approximately 14 psi. An exemplary operating parameter for cardiovascular catheter indications includes operating pressures ranging up to approximately 40 to 50 ATM (or about 588-735 PSI).

In accordance with another aspect, catheter further can include bellows, or a bladder component (not shown) within the chamber to prevent leaks. The bellows or bladder component is attached to the exterior surface of the inner tubular member and is in fluid communication with the fluid flow port, wherein fluid introduced through the fluid flow port expands the bellows component to further retract the outer tubular member.

In yet another aspect of the disclosed subject matter, spacer elements (not shown) can be provided within the pressure chamber. The spacer elements can prevent the outer tubular member, proximal seal and distal seal from being collapsed during delivery and storage of the catheter. The spacer elements can also reduce the amount of fluid needed to retract the outer tubular member. The spacer elements can be made of any of a variety of suitable shapes and materials, such as ring members having diameters corresponding to the inner and outer diameters of the inner and outer tubular members, respectively.

If desired, the distal seal can form a bumper or stop member for the medical device. Alternatively, in accordance with another aspect of the disclosed subject matter, the catheter can include a stop 710 secured to the inner tubular member 110, as depicted in FIGS. 7 and 8. The stop is disposed distal to the pressure chamber 450 and proximal to the medical device to be delivered, e.g., the stent. In this manner, the stop 710 seals the hydraulic fluid lumen 310 but allows the guidewire tube 321 and/or guidewire (not shown) to pass through. Stop 710 can be made of or include a radiopaque material to provide the physician performing the procedure with visibility as to placement of the catheter so that the medical device can accurately be positioned at the treatment site. The stop 710 is thus a radiopaque marker. For example, the marker can be a radiopaque metallic ring, or made of a tungsten loaded polymer for increased softness and flexibility. Other suitable markers known can be used. In other embodiments, the pressure chamber 450 is spaced from the medical device to be delivered, as further discussed herein.

In accordance with another aspect of the disclosed subject matter, other features, such as a spring, can be provided to bias the outer tubular member 120 in the proximal direction P. Examples of springs and other features that can be implemented with embodiments of the subject matter can be found in U.S. application Ser. No. 13/467,660, entitled "Catheter having Hydraulic Actuator" by Michael Bialas and Michael Green and owned by Abbott Cardiovascular Systems Inc.; U.S. application Ser. No. 13/467,679, entitled "Catheter having Dual Balloon Hydraulic Actuator" by Michael Green and Michael Bialas and owned by Abbott Cardiovascular Systems Inc.; and U.S. application Ser. No. 13/467,715, entitled "Catheter having Hydraulic Actuator with Tandem Chambers" by Michael Green and Michael Bialas, the contents of which are herein incorporated by reference in their entirety.

Reference is now made to FIG. 6, solely for purposes of illustration, which depicts an over-the-wire variation of the disclosed subject matter. In this embodiment, catheter 100 includes inner tubular member 110, outer tubular member 120 (shown in a retracted position), a guidewire lumen 320, and fluid lumen 310 having fluid flow port 420. Catheter 100 further includes medical devices, such as stent 440 as shown in an expanded state, stent seat 510, and a distal guidewire port 430.

As shown in FIG. 6A, solely for the purpose of illustration, the inner tubular member 110 or elongated catheter shaft of the catheter can include first and second tubular members 110 and 610, respectively, in coaxial relationship with each other to define a central guidewire lumen 320 within the first tubular member 110 and an annular fluid lumen 310 located between the first and second tubular members 610 of the inner tubular member or shaft. The fluid lumen 310 can supply a hydraulic medium under positive pressure and can withdraw the hydraulic medium, i.e., provide negative pressure, from pressure chamber 450 as desired. The catheter is sized and configured for delivery within a corresponding body lumen for the intended indication, such as a vasculature for vascular intervention. The catheter includes a guidewire lumen for delivery over a guidewire 620 as shown in FIG. 6A. For example, in one embodiment such as for neuro indications, the catheter can be 0.012 or 0.010 guidewire compatible. The portion of the inner tubular member extending distal of the chamber can be defined by an extension of the first tubular member 110, or an extension of the second tubular member 610, or by a separate tubular member as desired. Although a coaxial shaft and over-the-wire (OTW) catheter configuration is depicted in FIG. 6, those skilled in the art will recognize that other configurations and known materials of construction can be used without departing from the scope of the disclosed subject matter, for example, the rapid exchange and/or dual lumen configurations as previously described.

Further in accordance with the disclosed subject matter, an actuator member and a lock mechanism also can be provided to prevent the outer tubular member of the catheter from prematurely moving in the proximal direction. For purpose of illustration and not limitation, reference is made to the catheter having one or more pressure chambers as describe above. The actuator member is disposed within the pressure chamber for movement between a first position and a second position. Additionally, the lock mechanism is disposed within the pressure chamber. The lock mechanism has an engaged condition to prevent movement of the outer tubular member relative the inner tubular member and a disengaged condition to allow movement of the outer tubular member. The lock mechanism is shifted to the disengaged position when the actuator is moved to the second position.

Figure 9:
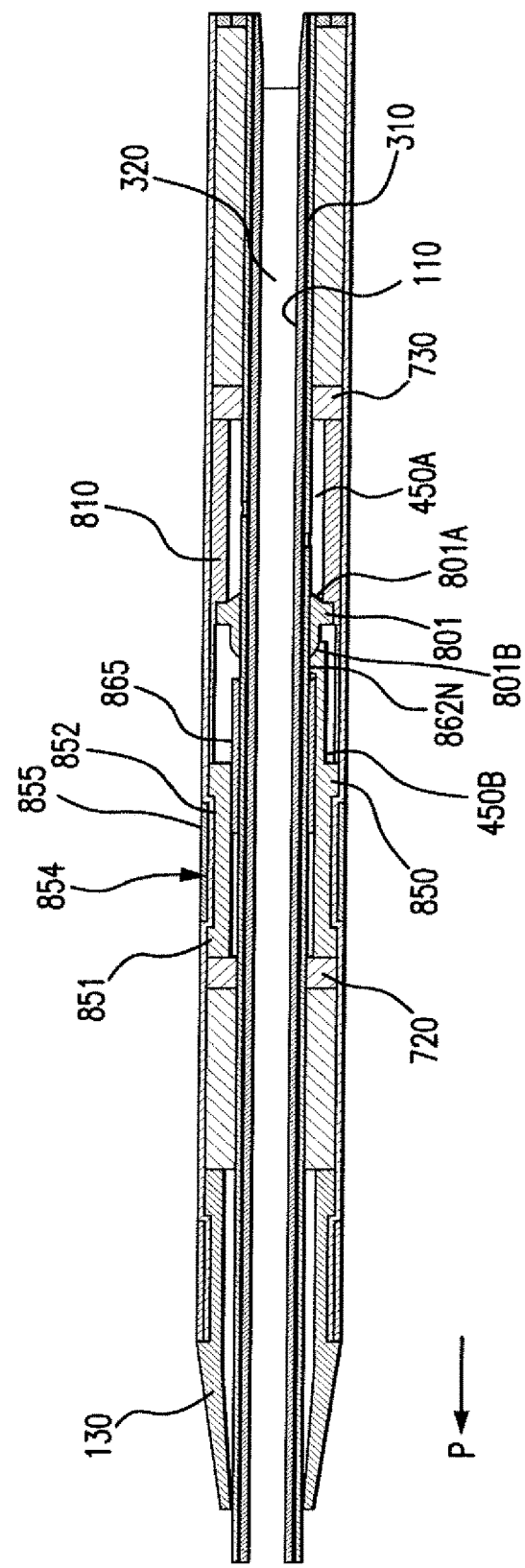
FIG. 9 is a cross sectional side view of the distal end portion of another embodiment of a catheter with an actuator and locking mechanism in an engaged condition, in accordance with the disclosed subject matter.

Reference is now made to the representative catheter embodiment of FIG. 9 which depicts a locking system according to one embodiment of the disclosed subject matter. The locking system includes an actuator member 801 disposed within the pressure chamber 450, as depicted. The actuator member 801 is movable between a first position and a second position. The actuator member 801 includes a seal section 801A and a cam section 801B.

Figure 10A:
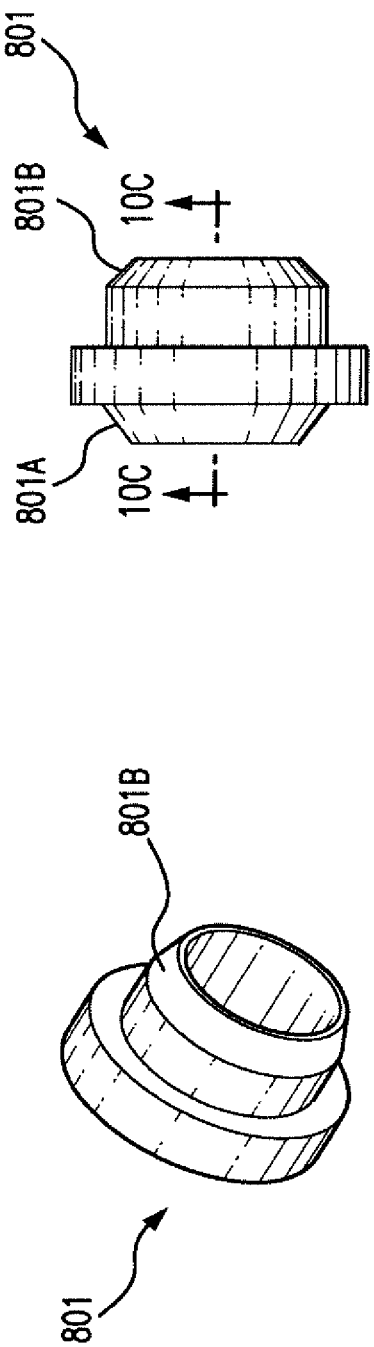
FIG. 10A is a perspective view of an actuator member.
Figure 10B:
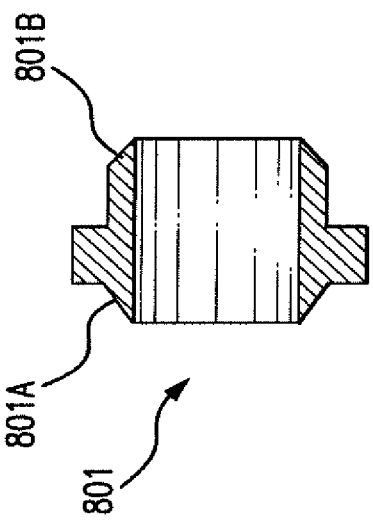
FIG. 10B is a side view of the actuator member of FIG. 10A.
Figure 10C:
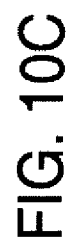
FIG. 10C is a cross section of the actuator member of FIG. 10B, in accordance with the disclosed subject matter.

With reference now to FIGS. 10A-10C, an exemplary embodiment of an actuator member 801 of the disclosed subject matter is depicted. Generally, as depicted in the perspective view of FIG. 10A, the actuator member 801 is in cylindrical form and capable of movement along the exterior surface of the inner tubular member. As shown in FIG. 10B, the seal section 801A depicted herein is formed as a radially-outward extending flange, although other configurations can be used. The cam section 801B is formed as an angled surface disposed at the proximal end of the actuator member. The cam surface can be formed as an angle, such as between about 10° to about 45° with respect to the longitudinal axis. Alternatively, the cam can be a continuous surface or the like. Additionally, the actuator member can be provided with a wiper seal or similar configuration of the reduced inner diameter along one or both ends to form a seal with the exterior surface of the inner tubular member. The actuator member can be made of any suitable material capable of performing as desired. For example, a class 6 medical material having a durometer ranging from approximately 50 to about 90 can be used for cardiovascular indication.

With reference back to FIG. 9, a stop member 810 can be disposed between the outer tubular member 120 and the inner tubular member 110. For example and as embodied herein, the stop member 810 can comprise a free-floating member, such as a sleeve movable relative the outer tubular member 120. The stop member 810 can be disposed distal to the actuator member 801 to define the first position of the actuator member 801 relative the fluid flow port 420. As depicted in FIG. 9, the stop member 810 separates the actuator member 801 from the distal seal 730 and the actuator member 801 disposed initially is proximal to the fluid flow port 420 in the first position. The stop member 810 defines one or more ledges or steps of increasing inner diameter in the proximal direction, as shown in FIG. 9. Any suitable member can be used for the stop member 810, such as a bushing. When the actuator member 801 is in the first position, the seal section 801A of the actuator member abuts a ledge or the stop member 810 to form a seal with the outer tubular member 120 and the inner tubular member 110. The seal created by the seal section 801A of the actuator member 801 defines a distal chamber portion 450A and a proximal chamber portion 450B within the pressure chamber 450. The stop member 810 is disposed in the distal chamber 450A when the actuator is in the first position.

As fluid is introduced through the fluid flow port 420 and into the distal chamber portion 450A of the pressure chamber 450, a force is applied on the seal section 801A to move the actuator member 801 from the first position toward the second position in the proximal direction P. When the actuator member 801 moves toward the second position, the actuator member 801 becomes spaced from the stop member 810 and the seal created by the seal section 801A is disrupted. Accordingly, the proximal movement of the actuator member 801 causes the distal chamber portion 450A and the proximal chamber portion 450B to be in fluid communication with each other and the fluid introduced into the distal chamber portion 450B moves into the proximal chamber portion 450B. When the actuator member 801 is in the second position, fluid introduced through the fluid flow port 420 and into the pressure chamber 450 can now apply a force on the proximal seal 720.

As previously noted, and further depicted in FIG. 9, the locking system embodied herein further includes a lock mechanism 850 disposed between the exterior surface of the inner tubular member 110 and interior surface of the outer tubular member 120. The lock mechanism 850 in this embodiment is positioned proximal the actuator member 801. Generally, the lock mechanism 850 can include a body member 851 coupled with or otherwise secured to the outer tubular member 120 as described in detail below. The lock mechanism also includes latch 862N having an engaged condition as depicted in FIG. 9 and a disengaged condition as depicted substantially in FIG. 12, and further described below.

For purposes of illustration and not limitation, reference is now made to FIGS. 11A-11E, which depict an exemplary embodiment of a lock mechanism of the disclosed subject matter. Generally, as depicted in the perspective view of FIG. 11A, the lock mechanism 850 includes a cylindrical body member 801 with recess 852 and at least one latch 863 extending from the body member 801. FIG. 11B depicts a side view of the lock mechanism 850 of FIG. 11A and FIG. 11C is a front view of the lock mechanism of FIG. 11A. For example, and as best shown in FIG. 11A and FIG. 11C, the lock mechanism 850 herein includes 3 latches 863 spaced about and extending distally from the body member 851. FIG. 11D is a cross section of the lock mechanism of FIG. 11B across lines 11D-11D and FIG. 11E is a detail view of the lock mechanism of FIG. 11D about line 11E. As depicted in FIG. 11B and FIG. 11D, each latch 863 can be formed at least in part by a cantilevered arm or the like with a hook projection 863A. As depicted in FIG. 11E, the distal end of each hook projection 863A can have an angled surface to be engaged by the cam section of the actuator member. The angled surface can be at a suitable angle alpha α, such as for example between 0° and 60°.

With reference again to FIG. 9, the body member 851 has a recess 852 defined in an outer surface of the body member 851 to assist with securing the lock mechanism 850 to the outer tubular member 120. During assembly, the lock mechanism can be coupled with or secured to the outer tubular member 120. For example, the outer tubular member 120 can be received within the recess 852 to form a trough 854 along a portion of an exterior surface of the outer tubular member 120. A filler 855 can be disposed in the trough 854 of the outer tubular member 120 within the recess 852 to couple the outer tubular member 120 to the body member 851 of the lock mechanism 850. Furthermore, the filler can be provided with additional hoop strength to secure the portion of outer tubular member within the recess of the lock mechanism, as disclosed in the currently pending application entitled, "Catheter Having Movable Tubular Structure", assigned to Abbott Cardiovascular Systems Inc. and filed on the same day as the present application, the contents of which are incorporated by reference herein in its entirety. The filler can abut the lock mechanism with the outer tubular member sandwiched therebetween to create the grip and lock.

The filler can be any suitable material capable of providing sufficient hoop strength to couple the outer tubular member with the recess of the lock mechanism. For example, the filler can comprise at least one of nylon, a fluoropolymer such as Kynar, PEEK, epoxy, platinum iridium, ceramic or metal, such as a metal band or the like. In accordance with a particular aspect of the disclosed subject matter, filler can comprise a material compatible for bonding with a material of the outer tubular member. For example, the material of the filler can comprise the same material as the outer tubular member. The compatibility of the filler and the outer tubular member thus allows for a more secure lock between the outer tubular member and the lock mechanism, even if the outer tubular member is not thermally compatible with the lock mechanism. Additionally, the increased thickness of outer tubular member and filler bonded together with the recess provides a strength that a single layer material does not inherently comprise. Further, a substantially continuous surface of the adjacent outer tubular member with the filler is provided by the heat bond to eliminate an area or edge that could potentially catch while the system is being advanced or withdrawn from the vasculature. Additionally, the lock created by the filler provides the strength to maintain the integrity of the catheter components. The filler thus can bonded to the outer tubular member by at least one of heat bonding, thermal bonding, adhesive bonding, or the like, as well as by crimping or swaging of a bond of suitable material.

With reference again to FIG. 9, the locking system can further include a sleeve 865 coupled to the inner tubular member 110. The sleeve 865 is disposed between the inner tubular member 110 and the lock mechanism 850 and defines a ledge or engagement edge at its distal end. As depicted in FIG. 9, the hook projection 863A of the latch 863 is configured to engaged the edge of the sleeve 865 when in the engaged condition. Alternative arrangements can be provided to form an engagement edge on the inner tubular member for engagement by the latch. For example, the inner tubular member can be provided within a ring or a projection, or a slot can be defined in an exterior surface of the inner tubular member. Any suitable material can be used for the sleeve.

Figure 12:
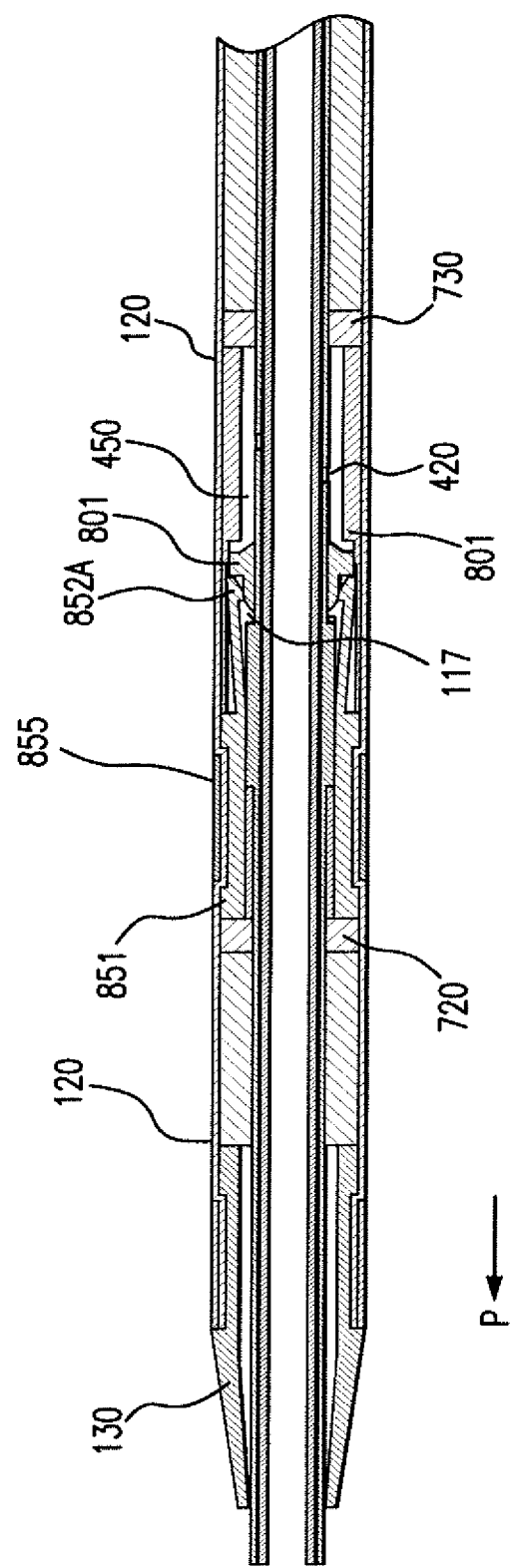
FIG. 12 is a cross sectional side view of a catheter with the lock mechanism in a disengaged condition.

FIG. 12 shows an embodiment of the subject matter with the latch 863 in the disengaged condition. When the actuator member 801 is moved to the second position as previously described, the cam section 801B of the actuator member 801 engages the latch 863. Upon the force of the cam section 801B moving in the proximal direction P, due to hydraulic pressure acting on the seal section of the actuator member 801, the latch 863 is then shifted to the disengaged condition by the cam section 801B and thus releases from the sleeve or other engagement edge provided for subsequent movement of the outer tubular member in the proximal direction.

In the embodiment of FIG. 12, the sleeve is replace by a slot 117 defined in the exterior surface of the inner tubular member 110 for purpose of illustration. In this embodiment, the latch 863 is engaged with the slot 117 when in the engaged condition. As depicted in the embodiment of FIG. 12, the cam section 801B of the actuator member 801 disengages the latch 863 when the actuator member 801 is moved toward the second position, to release the outer tubular member for subsequent movement in the proximal direction by the fluid pressure acting on the proximal seal.

The lock mechanism can be made of or comprise any suitable biocompatible material, such as PEEK. Because it is not necessary to bond the outer tubular member directly to the lock mechanism, the lock mechanism, and more specifically the body member of the lock mechanism, can comprise a material incompatible for thermal bonding with the material of the outer tubular member. As such, it is beneficial for the lock mechanism to be made of a suitable material having a higher melt temperature than that of the outer tubular member and/or filler. Thus, even upon application of thermal energy or heat to the area of the lock mechanism, the lock mechanism can maintain its structural integrity. The lock mechanism can further include a PTFE liner or other low friction or lubricious layer, if desired.

In accordance with another aspect of the disclosed subject matter, a method of deploying a catheter is provided, comprising, among other things, providing a catheter as previously described above. The method further includes disposing a device, such as a stent, between the exterior surface of the inner tubular member and the interior surface of the outer tubular member at a location distal to the distal seal. The location of the device, such as a stent, along the catheter will depend on the desired indication such as cardiovascular intervention or peripheral intervention. Fluid is introduced through the fluid flow port and into the pressure chamber to move the actuator member toward the second position and to shift the latch of the lock mechanism to the disengaged condition. With the actuator member in the second position and the latch in the disengaged condition, fluid introduced through the fluid flow port and into the pressure chamber applies a force on the proximal seal of the pressure chamber to urge the outer tubular member in a proximal direction. As the outer tubular member is urged in the proximal direction, the stent is exposed and deployed in the luminal system of a patient. Upon deployment of the stent, the catheter is withdrawn from the luminal system. Additional details and feature regarding the method are described and/or understood from the description above, or otherwise incorporated by reference.

In accordance with the embodiments of the subject matter previously described, the components of the catheter can be made out of a plurality of suitable materials. For instance, the proximal and distal seals of the expandable chamber configuration can be formed of any suitable materials. Solely for example, the seals can be rubber or silicon. In embodiments having an expandable pressure chamber, the seals can be formed of a low durometer rubber having a compressed condition and an expanded condition. The seals can be significantly compressed and deformed in the initial delivery configuration, transitioning to the expanded condition when the pressure chamber is pressurized. Alternatively, the seals can be made of hydrophilic polymers that absorb fluid in the pressure chamber and expand along with the outer tubular member. Alternatively, the proximal and distal seals can be made of hydrophobic material.

The inner tubular member and outer tubular member each can be a single piece construction, or an assembly of components, and can be made of any suitable material. For example, suitable materials include, but are not limited to polymer materials such as nylon, urethane, polyurethane, PEEK, PTFE, PVDF, fluoropolymer such as Kynar, PE, HDPE, a trilayer material including L25, Plexar, PEBAX, or polyethylene of various suitable densities. In one example, the outer tubular member comprises a nylon braided tube with a PTFE liner. A lubricious liner, such as PTFE, on the inside diameter of the outer tubular member, or the sheath, allows the stent to deploy with low force and can prevent the outer tubular member from being bonded to the stent or other catheter components. In another example, the outer tubular member includes a fluoropolymer braided tube with lubricous liner. Furthermore, at least a portion of the inner and/or outer tubular members can be constructed of an alloy or metallic material, such as stainless steel hypodermic tubing or the like.

As a further alternative, the inner tubular member and/or the outer member each can be constructed of multiple outer tubular members. A stop can further form a joint for two adjacent tubular members. The outer tubular member can further be constructed of a composite comprising a fabrication of several different materials, such as a co-extrusion of different polymers, or a fiber-reinforced composite material such as fiber reinforced resin materials or braided materials. Solely for example, exemplary embodiments can include a braided tube with a PTFE liner, a Polymide middle layer with braiding and a Pebax 72D outer layer. Additionally, to improve flexibility, helical or spiral member configurations can be used in the construction of the inner and outer tubular members.

Exemplary constructions for the outer tubular member include a single layer of polyimide or PEEK; a trilayer material of L25, Plexar, HDPE; or a braided tube with a PTFE liner, a Polyimide middle layer braiding middle layer, and a Pebax 72D outer layer. The inner and/or outer tubular members can also be reinforced by the addition of a strengthening member, such as, for example, a wire coil. In one embodiment, the inner tubular member is reinforced by the addition of a strengthening member along a length corresponding to the pressure chamber.

It is further contemplated that the inner and outer tubular members can be constructed of other biocompatible material. As such, the inner and outer tubular members of the catheter can be constructed from the above-identified polymers, combinations or blends of these polymers, whether alone or in combination with other materials, or other bioabsorbable materials.

The inner and outer tubular members can be manufactured using a variety of known techniques such as but not limited to: extrusion, injection molding, air-blowing, stretching, deep drawing, polymerization, cross-linking, dipping from solution, powder depositioning, sintering, electrospinning, melt spinning, deformation under temperature, stretch blowing, chemical grafting any combination of the above with reinforcement element like metal braids, coils, glass fibers, carbon fibers and other kind of organic or inorganic fibers, liquid crystals, as well as classical machining technologies like milling, drilling, grinding, etc. In the event that metallic elements such as hypotubes are to be incorporated, various metallic manufacturing techniques can be used, such as but not limited to, machining, tube drawing processes, drilling, milling, EDM, other deformation methods, plating, sputtering, electrografting, sintering, and depositioning e-polishing, among others. In one embodiment of the disclosed subject matter, the inner tubular member includes a stainless steel hypotube at least at its proximal end.

Additionally, the inner and outer tubular members can be constructed from PE, polypropylene, Kynar, or urethane by an extrusion process using an extruder such as that available from any of a number of known suppliers. The materials can be post-processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

The inner and outer tubular members can be further coated with any of a variety of materials and techniques to enhance performance if desired, including a number of suitable coatings and coating techniques subject to patent matters owned by Abbott Laboratories such as U.S. Pat. Nos. 6,541,116, 6,287,285, and 6,541,116, the entireties of which are hereby incorporated by reference. For example, possible coating materials include lubricious materials such as Teflon®, and hydrophobic materials such as silicone lubricant dispersion PN 4097, or hydrophilic materials such as hydrogel, or lubricious coatings.

The inner and outer tubular members can have any suitable cross-sectional shape, including elliptical, polygon, or prismatic, although a circular cross-section generally is preferred. The inner and outer tubular members can also have any suitable size and diameter depending upon the desired application. The catheter is suitably sized and configured for delivery within a corresponding body lumen for the intended indication, such as a vasculature for vascular intervention.

As embodied herein, the outer tubular member can include an outer layer and an inner layer. The outer tubular member can be provided with an inner layer attached to or formed with an outer layer. The inner layer or liner can include a lubricious material to facilitate the sliding of the outer tubular member in a proximal direction when the outer tubular member is retracted. For example, different types of polymers such as PTFE or any fluoropolymer and high-density polyethylene (HDPE) can be used for the inner layer or coated one on another. Additionally, other lubricious polymers can be used. The outer layer, as embodied herein, provides sufficient strength to capture a medical device therein, as well as allow movement between the first position and the second position. The multiple layers can be formed separately and adhered or bonded together or co-extruded as a single member.

In further accordance with the disclosed subject matter the outer tubular member can include a reinforcing layer disposed between the outer layer and the inner layer, such as a braided material. For example, the reinforcing layer can be provided in the form of a braided stainless steel tube or sheet or the like. The braid can include flattened filaments, as opposed to having filaments with a round cross-section. Alternatively, the reinforcement can be in the form of a tube including woven fabric or appropriately oriented filaments, such as carbon fibers encased in a polymeric matrix. Likewise, such reinforcing fibers could additionally or alternatively be incorporated into inner layer and/or outer layer during the manufacturing process.

When the outer tubular member is provided with an inner layer, outer layer and a reinforcing layer, the outer tubular member can be formed in the following manner. First, inner layer is formed through a tubular extrusion process, and disposed about a forming mandrel (not shown). The forming mandrel, as embodied herein, has a shape that corresponds to the desired shape of the inside of the outer tubular member. Next, the reinforcing layer, which can be provided in the form of a stainless steel braid material, is positioned over a predetermined length of inner layer. Next, the outer layer is extruded and positioned over the reinforcing layer. The outer layer can be provided in the form of two separate tubular members that are overlapped slightly at their ends over reinforcing layer. Each portion of outer layer can be a different material selected to provide a different durometer as described above. The two portions of outer layer can overlap by an amount such as approximately 0.1 inches. Next, a sleeve of heat shrinkable material is positioned over the entire outer tubular member assembly. Finally, heat is applied to the assembly. When heat is applied, the heat shrinkable tubing shrinks, and causes inner layer to fuse with outer layer, trapping reinforcing layer therebetween. The heating process also causes inner layer to conform to the shape of the forming mandrel. After the assembly cools, the heat shrinkable tubing is cut away, leaving behind the outer tubular member.

While the disclosed subject matter is described herein in terms of certain preferred embodiments, those skilled in the art will recognize that various modifications and improvements can be made to the disclosed subject matter without departing from the scope thereof. Additional features known in the art likewise can be incorporated, such as disclosed in U.S. Pat. No. 7,799,065 to Pappas, which is incorporated in its entirety by reference herein. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Furthermore, although reference is made to a stent throughout this disclosure, other suitable devices and implants likewise can be delivered using the catheter and system disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A catheter comprising:
    an inner tubular member having a proximal end portion, a distal end portion and an exterior surface, the inner tubular member further having a fluid lumen defined therein, the fluid lumen having a fluid flow port defined by the exterior surface along the distal end portion of the inner tubular member;
    an outer tubular member movable relative to the inner tubular member, the outer tubular member having a proximal end, a distal end and an interior surface directed toward the exterior surface of the inner tubular member;
    a proximal seal extending from the interior surface of the outer tubular member toward the exterior surface of the inner tubular member, the proximal seal located proximal to the fluid flow port;
    a distal seal extending from the exterior surface of the inner tubular member toward the interior surface of the outer tubular member, the distal seal located distal to the fluid flow port;
    a pressure chamber defined by the proximal seal, the distal seal, the exterior surface of the inner tubular member, and the interior surface of the outer tubular member;
    an actuator member disposed within the pressure chamber, the actuator member having a seal section and a cam section, the actuator member being moveable between a first position and a second position, wherein fluid introduced through the fluid flow port and into the pressure chamber applies a force on the seal section to move the actuator member from the first position toward the second position; and
    a lock mechanism disposed between the exterior surface of the inner tubular member and the interior surface of the outer tubular member, the lock mechanism including a latch having an engaged condition to prevent movement of the outer tubular member relative the inner tubular member and a disengaged condition to allow movement of the outer tubular member relative the inner tubular member, the latch being shifted to the disengaged condition by the cam section when the actuator member is moved to the second position,
    wherein, with the actuator member in the second position and the latch in the disengaged condition, fluid introduced through the fluid flow port and into the pressure chamber applies a force on the proximal seal to urge the outer tubular member in a proximal direction.

2. The catheter according to claim 1, wherein the lock mechanism includes a body member and the latch is defined at least in part by an arm extending from the body member.

3. The catheter according to claim 2, wherein the lock mechanism includes a sleeve coupled to the inner tubular member, wherein the latch is engaged with the sleeve when in the engaged condition.

4. The catheter according to claim 3, wherein the cam section of the actuator member disengages the latch from the sleeve when the actuator member is moved toward the second position.

5. The catheter according to claim 1, wherein a slot is defined in the exterior surface of the inner tubular member, the latch engaged with the slot when in the engaged condition.

6. The catheter according to claim 1, further comprising a stop member being disposed between the outer tubular member and the inner tubular member to define the first position of the actuator member relative the fluid flow port.

7. The catheter according to claim 6, wherein the stop member comprises a sleeve movable relative the outer tubular member.

8. The catheter according to claim 7, wherein the actuator member moves in the proximal direction from the first position toward the second position.

9. The catheter according to claim 6, wherein the seal section of the actuator member forms a seal with the stop member to define a distal chamber portion and a proximal chamber portion within the pressure chamber when the actuator member is in the first position.

10. The catheter according to claim 9, wherein the distal chamber portion and the proximal chamber portion are in fluid communication with each other when the actuator member moves in the proximal direction from the stop member to disrupt the seal therebetween.

11. The catheter according to claim 1, wherein the lock mechanism includes a body member secured to the outer tubular member.

12. The catheter according to claim 11, wherein the body member comprises a material incompatible for thermal bonding with the material of the outer tubular member.

13. The catheter according to claim 1, wherein the outer tubular member comprises a nylon braided tube with a PTFE liner or a fluoropolymer braided tube with lubricous liner such as PTFE.

14. The catheter according to claim 1, wherein the inner tubular member further includes a guidewire lumen defined therein.

15. The catheter according to claim 1, further comprising a stent seat disposed along the inner tubular member distal to the pressure chamber and a stent positioned at the stent seat.

16. The catheter according to claim 15, wherein a distal end of the inner tubular member further comprises a distal tip disposed distal to the stent seat.

17. The catheter according to claim 1, further comprising at least one movable tubular structure coupled to the outer tubular member and disposed at least one of the proximal end of the outer tubular member or the distal end of the outer tubular member.

18. A method of deploying a catheter, comprising:
   providing a catheter including:
   an inner tubular member having a proximal end portion, a distal end portion and an exterior surface, the inner tubular member further having a fluid lumen defined therein, the fluid lumen having a fluid flow port defined by the exterior surface along the distal end portion of the inner tubular member,
   an outer tubular member movable relative to the inner tubular member, the outer tubular member having a proximal end, a distal end and an interior surface directed toward the exterior surface of the inner tubular member,
   a proximal seal extending from the interior surface of the outer tubular member toward the exterior surface of the inner tubular member, the proximal seal located proximal to the fluid flow port,
   a distal seal extending from the exterior surface of the inner tubular member toward the interior surface of the outer tubular member, the distal seal located distal to the fluid flow port,
   a pressure chamber defined by the proximal seal, the distal seal, the exterior surface of the inner tubular member, and the interior surface of the outer tubular member,
   an actuator member disposed within the pressure chamber, the actuator member having a seal section and a cam section, the actuator member being moveable between a first position and a second position, wherein fluid introduced through the fluid flow port and into the pressure chamber applies a force on the seal section to move the actuator member from the first position toward the second position, and
   a lock mechanism disposed between the exterior surface of the inner tubular member and the interior surface of the outer tubular member, the lock mechanism including a latch having an engaged condition to prevent movement of the outer tubular member relative the inner tubular member and a disengaged condition to allow movement of the outer tubular member relative the inner tubular member, the latch being shifted to the disengaged condition by the cam section when the actuator member is moved to the second position;
   disposing a device between the exterior surface of the inner tubular member and the interior surface of the outer tubular member at a location distal to the distal seal; and
   introducing fluid through the fluid flow port and into the pressure chamber to move the actuator member toward the second position and shift the latch of the lock mechanism to the disengaged condition, wherein, with the actuator member in the second position and the latch in the disengaged condition, fluid introduced through the fluid flow port and into the pressure chamber applies a force on the proximal seal to urge the outer tubular member in a proximal direction.

* * * * *